United States Patent
Zhao et al.

(10) Patent No.: US 8,565,499 B2
(45) Date of Patent: Oct. 22, 2013

(54) METHODS, SYSTEMS, AND COMPUTER READABLE MEDIA FOR SYNTHETIC WAVELENGTH-BASED PHASE UNWRAPPING IN OPTICAL COHERENCE TOMOGRAPHY AND SPECTRAL DOMAIN PHASE MICROSCOPY

(75) Inventors: Mingtao Zhao, Durham, NC (US); Hansford Hendargo, Durham, NC (US); Joseph A Izatt, Raleigh, NC (US)

(73) Assignee: Duke University, Durham, NC (US)

( * ) Notice: Subject to any disclaimer, the term of this patent is extended or adjusted under 35 U.S.C. 154(b) by 899 days.

(21) Appl. No.: 12/460,532

(22) Filed: Jul. 21, 2009

(65) Prior Publication Data

US 2010/0150467 A1 Jun. 17, 2010

Related U.S. Application Data

(60) Provisional application No. 61/135,495, filed on Jul. 21, 2008.

(51) Int. Cl.
G06K 9/00 (2006.01)
G06K 9/40 (2006.01)

(52) U.S. Cl.
USPC .......................................... 382/128; 382/254

(58) Field of Classification Search
USPC ........ 382/128–132, 254; 250/455.11, 227.19, 250/227.27; 356/477, 479, 489, 497, 456
See application file for complete search history.

(56) References Cited

U.S. PATENT DOCUMENTS

| | | | |
|---|---|---|---|
| 4,052,889 A | 10/1977 | Mucciardi et al. | |
| 5,588,435 A | 12/1996 | Weng et al. | |
| 5,994,690 A * | 11/1999 | Kulkarni et al. | 250/216 |
| 6,618,152 B2 * | 9/2003 | Toida | 356/479 |
| 6,887,231 B2 | 5/2005 | Mrochen et al. | |
| 6,940,557 B2 | 9/2005 | Handjojo et al. | |

(Continued)

FOREIGN PATENT DOCUMENTS

| EP | 2427723 | 3/2012 |
|---|---|---|
| WO | WO 2010-129544 | 11/2010 |

OTHER PUBLICATIONS

Hirwnvwefwe et a;, Overcoming the 2it ambiguity in low coherence interferometric differential phase measurements, Proc. SPIE vol. 4251, p. 81-85, Coherence Domain Optical Methods in Biomedical Science and Clinical Applications, 2001.*

(Continued)

Primary Examiner — Andrae S Allison
(74) Attorney, Agent, or Firm — Jenkins, Wilson, Taylor & Hunt, P.A.

(57) ABSTRACT

In accordance with this disclosure, methods, systems, and computer readable media for synthetic wavelength-based phase unwrapping in optical coherence tomography are provided. Synthetic wavelength phase unwrapping can be applied to OCT data and can correctly resolve sample motions that are larger than $\lambda_o/2$. A method for phase unwrapping of an OCT signal can include acquiring raw OCT signal data, interpolating and processing the OCT signal data to obtain a DC spectrum, comparing the raw OCT signal data to the DC spectrum to generate an interference signal, applying Gaussian windows to the interference signal to generate a two separate signals, extracting phase information from the two signals, and comparing the phase information of the two signals to produce unwrapped phase data. A value of $2\pi$ can be added to the phase data if the difference between the phase information of the two signals is less than zero.

12 Claims, 9 Drawing Sheets

(56) References Cited

U.S. PATENT DOCUMENTS

| | | | |
|---|---|---|---|
| 7,092,748 B2* | 8/2006 | Valdes Sosa et al. | 600/407 |
| 7,102,756 B2* | 9/2006 | Izatt et al. | 356/479 |
| 7,187,800 B2* | 3/2007 | Hibbard | 382/173 |
| 7,330,270 B2* | 2/2008 | O'Hara et al. | 356/479 |
| 7,486,406 B2 | 2/2009 | Kim | |
| 7,602,500 B2 | 10/2009 | Izatt | |
| 7,719,692 B2 | 5/2010 | Izatt | |
| 7,796,243 B2* | 9/2010 | Choo-Smith et al. | 356/72 |
| 7,990,541 B2 | 8/2011 | Izatt | |
| 8,149,418 B2* | 4/2012 | Tearney et al. | 356/479 |
| 2005/0057756 A1* | 3/2005 | Fang-Yen et al. | 356/497 |
| 2005/0171438 A1* | 8/2005 | Chen et al. | 600/476 |
| 2007/0258094 A1* | 11/2007 | Izatt et al. | 356/456 |
| 2009/0185166 A1 | 7/2009 | Oldenburg et al. | |
| 2009/0270738 A1 | 10/2009 | Izatt | |
| 2011/0032533 A1 | 2/2011 | Izatt | |
| 2012/0188555 A1 | 7/2012 | Izatt | |

OTHER PUBLICATIONS

Hendargo et al, Synthetic Wavelength-Based Phase Unwrapping in Fourier Domain Optical Coherence Tomography, Optics Express, vol. 17, Issue 7, pp. 5039-5051 (2009) http://dx.doi.org/10.1364/OE.17.005039.*

O. W. Richards, "Phase Difference Microscopy," Nature, 1944, vol. 154, No. 672.

C. R. Tilford, "Analytical procedure for determining lengths from fractional fringes," Appl. Opt. 16, 1977, pp. 1857-1860.

Y. Cheng and J. C. Wyant, "Two-wavelength phase shifting interferometry," Appl. Opt. 23, 1984, pp. 4539-4543.

K. Creath, "Phase-shifting speckle interferometry," Appl. Opt. 24, 1985, pp. 3053-3058.

H. Gundlach, "Phase contrast and differential interference contrast instrumentation and applications in cell, developmental, and marine biology," Opt. Eng. 32, 1993, pp. 3223-3228.

E. Cuche, F. Bevilacqua, and C. Depeursinge, "Digital Holography for quantitative phase-contrast imaging," Opt. Lett. 24, 1999, pp. 291-293.

C.K. Hitzenberger, M. Sticker, R. Leitgeb, and A.F. Fercher, "Differential phase measurements in low-coherence interferometry without $2\pi$ ambiguity," Opt. Lett. 26, 2001, pp. 1864-1866.

C. Yang, A. Wax, R.R. Dasari, and M.S. Feld, "$2\pi$ ambiguity-free optical distance measurement with subnanometer precision with a novel phase-crossing low-coherence interferometer," Opt. Lett. 27, 2002, pp. 77-79.

Ding et al., "Real-time phase-resolved optical coherence tomography and optical Doppler tomography." Optics Express, Mar. 2002, vol. 10 No. 5.

R. Tripathi, N Nassif, J. S. Nelson, B. H. Park, and J. F. De Boer, "Spectral shaping for non-Gaussian source spectra in optical coherence tomography," Opt. Lett. 27, 2002, pp. 406-408.

Westphal, Volker et al., "Correction of Geometric and Refractive Image Distortions in Optical Coherence Tomography Applying Fermat's Principle," Optics Express, May 6, 2002, pp. 397-404, vol. 10, No. 9.

J. Gass, A. Dakoff, and M. K. Kim, "Phase imaging without $2\pi$ ambiguity by multiwavelength digital holography," Opt. Lett. 28, 2003, pp. 1141-1143.

J.F. De Boer, B. Cense, B. H. Park, M. C. Pierce, G. J. Tearney, and B. E. Bouma, "Improved signal-to-noise ratio in spectral-domain compared with time-domain optical coherence tomography," Opt. Lett. 28, 2003, pp. 2067-2069.

M. A. Choma, M. V. Sarunic, C. Yang, and J. A. Izatt, "Sensitivity advantage of swept source and Fourier domain optical coherence tomography," Opt. Express 11, 2003, pp. 2183-2189.

R. Leitgeb, C. K. Hitzenberger, and A. F. Fercher, "Performance of Fourier domain vs. time domain optical coherence tomography," Opt. Express 11, 2003, pp. 889-894.

Zawadzki, Robert J. et al., "Three-Dimensional Ophthalmic Optical Coherence Tomography With a Refraction Correction Algorithm," SPIE, 2003, vol. 5140.

D.L. Marks, P.S. Carney, and S.A. Boppart, "Adaptive spectral apodization for sidelobe reduction in optical coherence tomography images," J. Biomed. Opt. 9, 2004, pp. 1281-1287.

G. Popescu, L. P. Deflores, J.C. Vaughan, K. Badizadegan, H. Iwai, R. R. Dasari, and M. S. Feld, "Fourier phase microscopy for investigation of biological structures and dynamics," Opt. Lett. 29, 2004, pp. 2503-2505.

Tang, Maolong, "Corneal Mean Curvature Mapping: Applications in Laser Refractive Surgery," Biomedical Engineering Center, 2004, Ohio State University.

Yun, S. et al., "Removing the depth-degeneracy in optical frequency domain imaging with frequency shifting," Optics Express, Oct. 4, 2004, vol. 12, No. 20.

C. Joo, T. Akkin, B. Cense, B. H. Park, and J. F. De Boer, "Spectral-domain optical coherence phase microscopy for quantitative phase-contrast imaging," Opt. Lett. 30, 2005, pp. 2131-2133.

C. J. Mann, L. Yu, C. Lo, and M. K. Kim, "High-resolution quantitative phase-contrast microscopy by digital holography," Opt. Express 13, 2005, pp. 8693-8698.

Davis, A.M. et al., "Heterodyne swept-source optical coherence tomography for complete complex conjugate ambiguity removal," Journal of Biomedical Optics, Nov./Dec. 2005, vol. 10, No. 6.

G. Popescu, T. Ikeda, C. A. Best, K. Badizadegan, R. R. Dasari, and M. S. Feld, "Erythrocyte structure and dynamics quantified by Hilbert phase microscopy," J. Biomed. Opt. 10, 2005, 060503.

M. A. Choma, A. K. Ellerbee, C. Yang, T. L. Creazzo, and J. A. Izatt, "Spectral-domain phase microscopy," Opt. Lett. 30, 2005, pp. 1162-1164.

T. Ikeda, G. Popescu, R. R. Dasari, and M.S. Feld, "Hilbert phase microscopy for investigating fast dynamics in transparent systems," Opt. Lett. 30, 2005, pp. 1165-1167.

M. A. Choma, A. K. Ellerbee, S. Yazdanfar, and J. A. Izatt, "Doppler flow imaging of cytoplasm streaming using spectral domain phase microscopy," J. Biomed. Opt. 11, 2006, 024014.

Sicam, Victor Arni D.P., "Spherical Aberration of the Anterior and Posterior Surfaces of the Human Cornea," J. Opt. Soc. Am. A, Mar. 2006, pp. 544-549, vol. 23, No. 3.

Tang, Maolong et al., "Measuring Total Corneal Power Before and After Laser in Situ Keratomileusis With High-Speed Optical Coherence Tomography," J. Cataract Refract Surg, Nov. 2006, pp. 1843-1850, vol. 32, No. 11

A. K. Ellerbee and J.A. Izatt, "Phase retrieval in low-coherence interferometric microscopy," Opt. Lett. 32, 2007, pp. 388-390.

A. K. Ellerbee, T. L. Creazzo, and J. A. Izatt, "Investigating nanoscale cellular dynamics with cross-sectional spectral domain phase microscopy," Opt. Express 15, 2007, pp. 8115-8124.

E. J. McDowell, A. K. Ellerbee, M. A. Choma, B. E. Applegate, and J. A. Izatt, "Spectral domain phase microscopy for local measurements of cytoskeletal rheology in single cells," J. Biomed. Opt., 2007, 04400.

J. Kuhn, T. Colomb, F. Montfort, F. Charrière, Y. Emery, E. Cuche, P. Marquet, and C. Depeursinge, "Real-time dual-wavelength digital holographic microscopy with a single hologram acquisition," Opt. Express 15, 2007, pp. 7231-7242.

N. Warnasooriya and M.K. Kim, "LED-based multi-wavelength phase imaging interference microscopy," Opt. Express 15, 2007, pp. 9239-9247.

Wang et al., "Three dimensional optical angiography." Optics Express, 2007, pp. 4083-4097, vol. 15 No. 7.

Wang, "Three-dimensional optical micro-angiography maps directional blood perfusion deep within microcirculation tissue beds in vivo," Phys. Med. Biol. 2007, pp. N531-N537, vol. 52.

N. Lue, W. Choi, G. Popescu, T. Ikeda, R. R. Dasari, K. Badizadegan, and M. S. Feld, "Quantitative phase imaging of live cells using fast Fourier phase microscopy," Appl. Opt. 46, 2007, pp. 1836-1842.

A. Khmaladze, A. Restrepo-Martinez, M.K. Kim, R. Castañeda, and A. Blandon, "Simultaneous Dual-Wavelength Reflection Digital Holography Applied to the Study of the Porous Coal Samples," Appl. Opt. 47, 2008, pp. 3203-3210.

(56) References Cited

OTHER PUBLICATIONS

D. L. Marks, S.C. Schlachter, A.M. Zysk, and S.A. Boppart, "Group refractive index reconstruction with broadband interferometric confocal microscopy," J. Opt. Soc. Am. A 25, 2008, pp. 1156-1164.

Erich Götzinger, Michael Pircher, Wolfgang Geitzenauer, Christian Ahlers, Bernhard.Baumann, Stephan Michels, Ursula Schmidt-Erfurth, and Christoph K. Hitzenberger,."Retinal pigment epithelium seqmentation by polarization sensitive optical coherence tomography," Opt. Express.

J.A. Izatt and M.A. Choma, "Theory of Optical Coherence Tomography," in Optical Coherence Tomography: Technology and Applications, W. Drexler and J.G. Fujimoto, eds, Springer, 2008.

R. M. Werkmeister, N. Dragostinoff, M. Pircher, E. Gotzinger, C. K. Hitzenberger, R. A. Leitgeb, and L. Schmetterer, "Bidirectional Doppler Fourier-domain optical coherence tomography for measurement of absolute flow velocities in human retinal vessels," Opt. Lett. 33, 2008, pp. 2967-2969.

S. Tamano et al., "Phase-shifting digital holography with a low-coherence light source for reconstruction of a digital relief object hidden behind a light-scattering medium," Applied Optics, 2008, pp. 953-959, vol. 45, No. 5, Optical Society of America.

Sarunic, Marinko et al., "Imaging the Ocular Anterior Segment With Real-Time, Full-Range Fourier-Domain Optical Coherence Tomography,"Arch. Opthal., Apr. 2008, pp. 537-542, vol. 126, No. 4.

Vergnole et al., "Common Path swept source OCT interferometer with artifact removal." Proc of SPIE, 2008, 8 pages, vol. 6847.

V. Srinivasan, B.K. Monson, M. Wojtkowski, R.A. Bilonick, I. Gorczynksa, R. Chen, J.S. Duker, J.S. Schumann, J.G. Fujimoto, "Characterization of Outer Retinal Morphology with High-Speed, Ultrahigh Resolution Optical Coherence Tomography," Investigative Ophthalmology and Visual Science 49, 2008, pp. 1571-1579.

H.C. Hendargo, M. Zhao, N. Shepard, and J.A. Izatt, "Synthetic wavelength based phase unwrapping in spectral domain optical coherence tomography," Opt. Express 17, 2009, pp. 5039-5051.

Jae Ho Han et al., "Common path fourier domain optical coherence tomography in ophthalmology applications," Life Science Systems and Applications Workshop, 2009, pp. 163-166.

Zhao, Mingtao et al., "Single-Camera Sequential-Scan-Based Polarization-Sensitive SDOCT for Retinal Imaging," Optics Letters, Jan. 15, 2009, pp. 205-207, vol. 34, No. 2.

International Search Report and Written Opinion for Application No. PCT/US2010/033540 dated Jul. 16, 2010.

Liu et al., "Compressive SD-OCT: the application of compressed sensing in spectral domain optical coherence tomography," Optics Express, 2010, pp. 22010-22019, vol. 18, Issue 21.

Non-Final Office Action for U.S. Appl. No. 12/386,945 dated Jul. 13, 2011.

Wieserlabs UG Data Sheet—1 GHz Dual-Balanced InGaAs Low Noise Photodetector No. WL-BPD1GA, www.wieserlabs.com, Oct. 2011.

Yogesh, Verma et al., "Use of common path phase sensitive spectral domain optical coherence tomography for refractive index measurements." Applied Optics, 2011, pp. E7-E12, vol. 50, Issue 25.

Final Office Action for U.S. Appl. No. 12/386,945 dated May 23, 2012.

Park et al., "Double common-path interferometer for flexible optical probe of optical coherence tomography," Optics Express, 2012, pp. 1102-1112, vol. 20, Issue 2.

Non-Final Office Action for U.S. Appl. No. 12/386,945 dated Mar. 19, 2013.

* cited by examiner

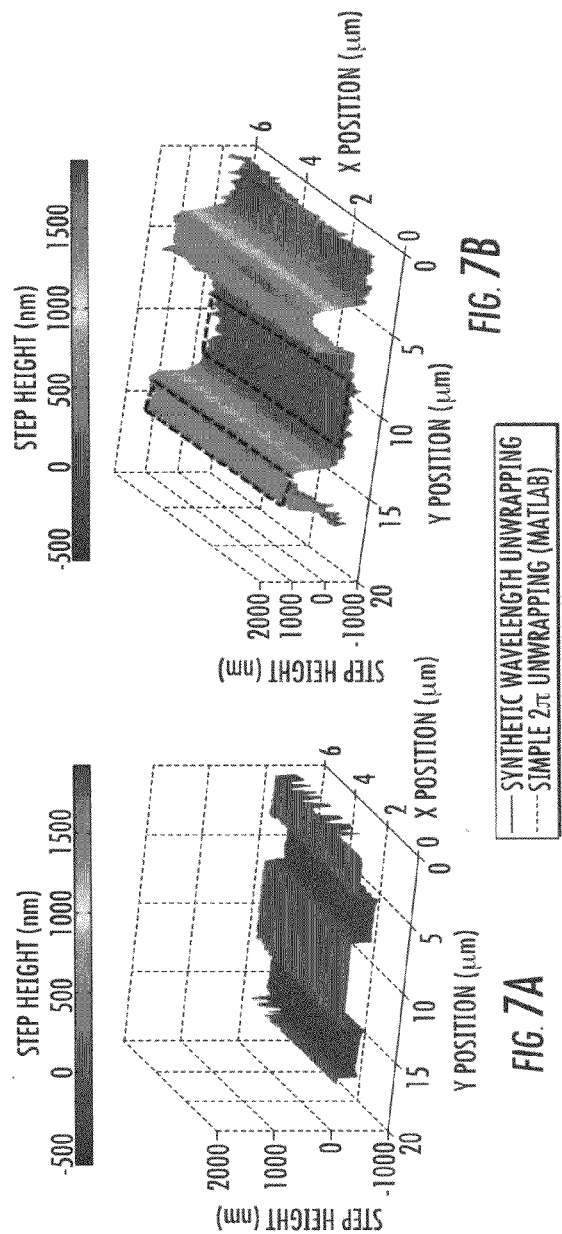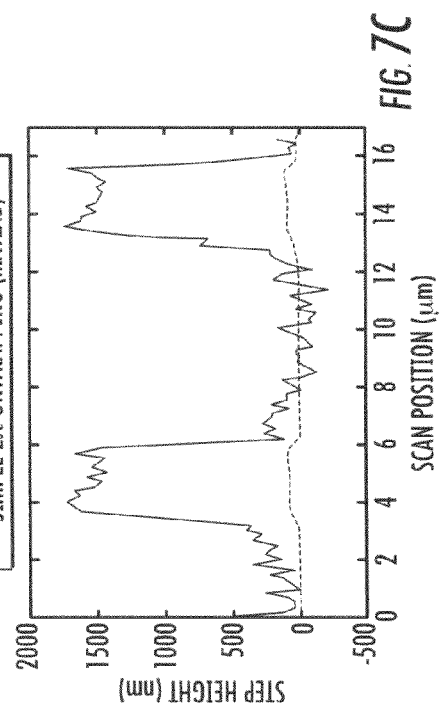
FIG. 7A
FIG. 7B
FIG. 7C

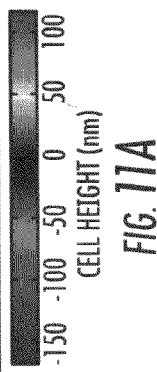
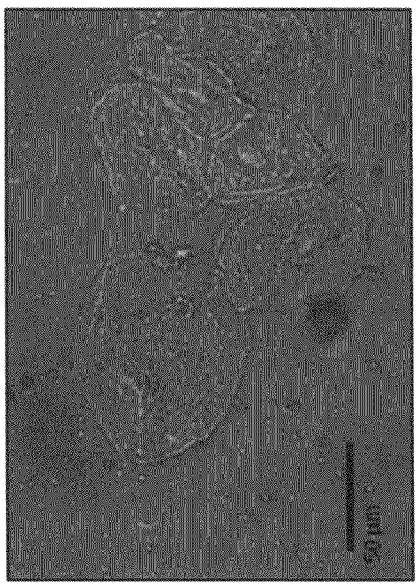
FIG. 11A
FIG. 11B
FIG. 11C

METHODS, SYSTEMS, AND COMPUTER READABLE MEDIA FOR SYNTHETIC WAVELENGTH-BASED PHASE UNWRAPPING IN OPTICAL COHERENCE TOMOGRAPHY AND SPECTRAL DOMAIN PHASE MICROSCOPY

RELATED APPLICATIONS

This application claims the benefit of U.S. Provisional Patent Application Ser. No. 61/135,495 filed Jul. 21, 2008, the disclosure of which is incorporated herein by reference in its entirety.

GOVERNMENT INTEREST

The invention was made with U.S. Government support under Grant No. R21 EB006338 awarded by United States National Institutes of Health. Thus, the U.S. Government has certain rights in the invention.

TECHNICAL FIELD

The subject matter described herein relates to phase imaging systems and techniques such as for use in biological research. More specifically, the subject matter relates to methods, systems, and computer readable media for use in optical coherence tomography and spectral domain phase microscopy.

BACKGROUND

Recently, there has been much interest in developing quantitative phase imaging techniques for use in biological research, particularly at the cellular level (e.g., detecting sub-wavelength dynamics in biological samples). Techniques such as phase contrast and differential interference contrast microscopy have been used to image transparent samples by converting phase differences to intensity differences. These methods offer qualitative information about sample structure but suffer from a non-linear phase to amplitude conversion, thus they are unable to provide quantitative data. There has been much work in recent years to develop quantitative phase imaging techniques capable of detecting sub-wavelength dynamics in biological samples.

For instance, techniques such as phase contrast and differential interference contrast microscopy have been used to image transparent samples qualitatively by converting phase differences to intensity differences, but these methods suffer from a non-linear phase to amplitude conversion and thus do not directly provide quantitative data. In addition, phase shifting interferometry, digital holography, Fourier phase microscopy, and Hilbert phase microscopy are interferometric techniques that are capable of detecting nanometer scale features in biological specimens. These quantitative methods have applications in the realm of cellular imaging due to their high sensitivity and use of intrinsic contrast agents, but they lack the ability to obtain depth-resolved measurements from an optically thick sample.

The development of Fourier-domain optical coherence tomography (FDOCT), particularly spectrometer-based spectral-domain systems with no moving parts (spectral-domain OCT or SDOCT), has greatly enhanced the phase stability of optical coherence tomography (OCT) systems due to improvements to the system signal-to-noise ratio (SNR) over time domain systems. Common path implementations have given rise to a new class of functional, nanometer-scale sensitive quantitative phase microscopies termed spectral domain phase microscopy (SDPM) or spectral domain optical coherence phase microscopy (SDOCPM). Other implementations of OCT including swept-source OCT (SSOCT), optical frequency-domain imaging (OFDI) also depend in some applications on phase unwrapping.

In SDPM, phase information is obtained from Fourier processing as in standard SDOCT. The phase of a given depth sample represents sub-coherence length changes in the optical path length through the sample as a function of time or a lateral dimension and can be caused by changes to the refractive index, position of scattering objects, or both. SDPM is capable of producing depth-resolved phase maps measuring the motion of a dynamic sample throughout its volume. Using a common path geometry allows for cancellation of common mode noise, and such systems have experimental phase sensitivities as low as 53 picometers. SDPM has been used to study cytoplasmic streaming in Amoeba using Doppler flow, cytoskeletal rheology, and contractile motion of beating cardiomyocytes. All the aforementioned phase imaging modalities can suffer from phase wrapping artifacts.

The phase in the OCT signal is linearly related to the sample motion over time. The measured phase is limited, however, to a range of $-\pi$ to $+\pi$. An artifact known as phase wrapping occurs when a change in phase between consecutive measurements is such that the total phase change falls outside this range and thus wraps to the opposite end of the range, yielding an ambiguous result. As SDPM operates in a reflection geometry, changes in a sample reflector's position greater than half of the source center wavelength will induce phase wrapping. In some cases, unwrapping the phase can be accomplished easily by adding or subtracting $2\pi$ to data points at jump discontinuities as long as the phase jump itself is no more than $2\pi$. However, if a jump greater than $2\pi$ is present, this simple algorithm is no longer sufficient to correctly unwrap the phase.

Software implementations for phase unwrapping techniques have been used in SDPM, but they are often complex and computationally intensive. For example, one technique to resolve the $2\pi$ ambiguity in low coherence interferometry used a dispersion imbalance in the sample arm and polarization effects to simultaneously detect two interferograms from different lateral locations on a sample. This method required two spectrometer channels as well as additional polarization optics, which add complexity to the optical setup.

The use of two or three illuminating wavelengths to perform more robust phase unwrapping was first introduced in phase shifting interferometry and has since been applied in digital holography and phase imaging interference microscopy. The difference in the phase information obtained at two or more wavelengths can be cast in terms of an equivalent phase that would be obtained at a longer synthetic wavelength, $\Lambda$, which is a function of each of the imaging wavelengths. This method allows wrap-free measurements of changes in optical path length less than $\Lambda/2$, which can be significantly larger than any of the imaging wavelengths alone. A similar technique using a combination of low coherence and continuous wave sources was used to detect phase crossings in a Michelson interferometer allowing for phase wrap removal. These techniques require the use of multiple sources, which also complicate the optical setup. A similar technique in broadband interferometric confocal microscopy measured the group optical path delay through a sample by detecting relative phase changes between different wavelengths, allowing for measurement of the group refractive index while avoiding phase ambiguity.

Accordingly, in light of these difficulties, a need exists for improved methods, systems, and computer readable media for phase unwrapping of an OCT signal.

SUMMARY

In accordance with this disclosure, methods, systems, and computer readable media for synthetic wavelength-based phase unwrapping in Fourier domain optical coherence tomography and spectral domain phase microscopy are provided. Synthetic wavelength phase unwrapping can be applied to OCT data and can correctly resolve sample motions that are larger than $\lambda_o/2$. According to one aspect of the presently disclosed subject matter, a method for phase unwrapping of an OCT signal can include acquiring raw OCT signal data, interpolating the raw OCT signal data to be evenly spaced in k, processing the interpolated OCT signal data to obtain a direct-current (DC) or background spectrum, comparing the raw OCT signal data to the DC spectrum to generate an interference signal, applying Gaussian windows to the interference signal to generate a first signal and a second signal, processing the first signal and the second signal, extracting phase information from each of the first signal and the second signal, and comparing the phase information of the first signal to the phase information of the second signal to produce unwrapped phase data. A value of $2\pi$ can be added to the phase data if the difference between the phase information of the first signal and the second signal is less than zero.

It is noted that image processing in OCT can use the Fourier transform of a broadband spectrum. By windowing the signal spectrum before applying the Fourier transform, phase information at multiple center wavelengths can be obtained. A similar procedure to the multi-wavelength method previously used in other phase imaging modalities may then be applied for correct phase unwrapping, except that in OCT only a single source is needed due to the large spectral bandwidth used. Windows can be centered at two different wavelengths to OCT spectra to measure and correctly unwrap quantitative phase data. Such a procedure can be applicable to other phase based implementations of OCT in both the Fourier or time domain, including Doppler, polarization sensitive, or common path implementations. In addition, the technique discussed herein can be readily extendable to more than two spectral windows (e.g., up to a limit of as many windows as there are resolvable wavelengths), and also to imaging systems with multiple non-contiguous sources.

In other aspects, the subject matter described herein for phase unwrapping of an OCT signal can be implemented using computer readable media to having stored thereon executable instructions that when executed by the processor of a computer control the processor to perform steps. Exemplary computer readable media suitable for implementing the subject matter described herein includes disk memory devices, programmable logic devices, and application specific integrated circuits. In one implementation, the computer readable medium may include a memory accessible by a processor. The memory can include instructions executable by the processor for implementing any of the methods for phase unwrapping of an OCT signal described herein. In addition, a computer readable medium that implements the subject matter described herein may be distributed across multiple physical devices and/or computing platforms.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

BRIEF DESCRIPTION OF THE DRAWINGS

The subject matter described herein will now be explained with reference to the accompanying drawings of which:

FIG. 7a is an OCT surface profile of wrapped phase data from an AFM calibration step grating;

FIG. 7b is an OCT surface profile of a synthetic wavelength phase image of the grating shown in FIG. 7a;

FIG. 7c is a cross-sectional profile taken across the center of the grating shown in FIGS. 7a and 7b comparing the synthetic wavelength unwrapping method according to an aspect of the subject matter described herein with that of a simple unwrapping method of the prior art;

FIG. 11a is a wrapped phase image of human epithelial cheek cells;

FIG. 11b is a filtered single wavelength phase map corrected using synthetic wavelength unwrapping according to an aspect of the presently disclosed subject matter; and FIG. 11c is a bright field microscopy image of the cells shown in FIGS. 11a and 11b.

DETAILED DESCRIPTION

Figure 1B:
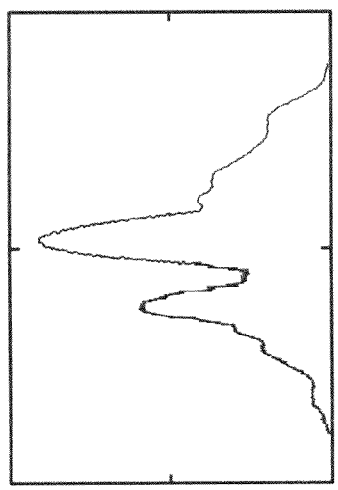
FIGS. 1a through 1d are graphs a broadband spectrum that is processed by a dual-wavelength unwrapping procedure according to an aspect of the subject matter described herein.
Figure 1C:
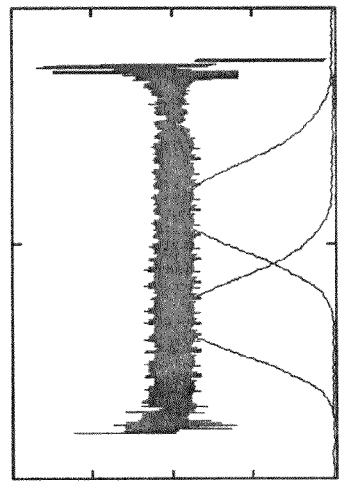
Figure 1A:
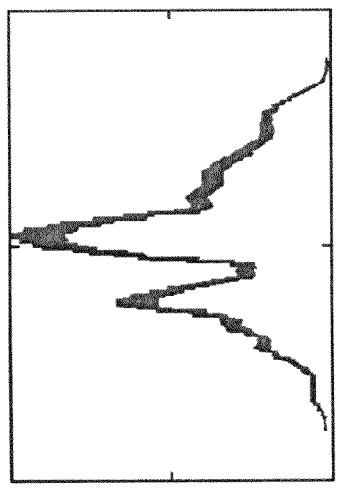
Figure 1D:
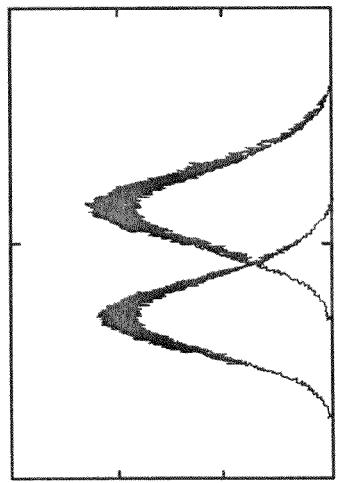

Methods, systems, and computer readable media are disclosed herein for synthetic wavelength-based phase unwrapping in Fourier domain optical coherence tomography.

A SD-OCT interferometric signal can be detected by a spectrometer. For the case of a single reflector, this interferometric signal can be given as a function of wavenumber by the following equation:

$$i(k) \propto S(k)\{R_R + R_S + \sqrt{R_R R_S}\cos(2kn(x+\Delta x))\}$$

where $S(k)$ is the source spectral density, $R_R$ and $R_S$ are the reference and sample reflectivities, respectively, n is the index of refraction, and $x+\Delta x$ is the distance between the reference and sample reflectors. The value x can account for the discrete sampling of the detector in the x-domain, while $\Delta x$ can represent subresolution changes in the sample position around x. It is noted that the first two terms in Eq. (1) represent DC terms while the third term contains the interferometric data of interest in OCT. Taking a Fourier transform of Eq. (1) and ignoring the DC terms can yield a depth reflectivity profile of the sample, known as an A-scan, with peaks located at $x=\pm 2nx$. These peaks can be described by the following relationship:

$$I(\pm 2nx) = S\sqrt{R_R R_S} E(2nx) \exp(\pm j2k_o n\Delta x) \tag{2}$$

in which S is the total source power, $E(2n\Delta x)$ is the coherence envelope function, $k_o$ is the source center wavenumber. The phase of the detected signal at time $t_n$ can be used to detect subresolution deviations in the sample with respect to the phase at a reference time, $t_o$. These deviations can be related to the detected phase as follows:

$$\Delta x_n = \frac{\lambda_0 \Delta \varphi_{t_j - t_0}}{4\pi n} + m \frac{\lambda_o}{2} \tag{3}$$

in which $\Delta x$ is the subresolution motion of the $n^{th}$-sample reflector, $\lambda_o$ is the center wavelength of the source, $\Delta \phi$ is the phase difference between times $t_j$ and $t_o$, and m is an integer number of half wavelengths. The factor of 2 in the denominator accounts for the double pass optical path length due to the reflection geometry of the optical setup that can be used in SDOCT. It is to be understood, however, that a given phase value is not an absolute determination of $\Delta x$, but it can potentially represent $\Delta x$ plus any integer number of half wavelengths. Without a priori knowledge of the sample motion or structure, there is no way to know the exact value of m in Eq. (3), as any displacement that is a multiple of $\lambda_o/2$ will induce phase wrapping. For instance, if $m=\pm 1$, simply adding or subtracting $2\pi$ to the phase can correctly unwrap the artifact. If $|m|\geq 2$, however, it will be impossible to unwrap the phase using this simple method. A larger $\Delta x$ can be correctly measured without phase wrapping if a larger $\lambda_o$ is used, which is a basis for multi-wavelength unwrapping in other phase imaging modalities and can be applied to OCT.

Accordingly, a system of dual wavelength phase unwrapping can be used to account for the uncertainty regarding the sample motion and/or structure. For two given wavelengths, $\lambda_1$ and $\lambda_2$, a longer synthetic wavelength $\Lambda$ can be defined as follows:

$$\Lambda = \frac{\lambda_1 \lambda_2}{|\lambda_1 - \lambda_2|} \tag{4}$$

The synthetic wavelength can have a corresponding synthetic phase, $\Delta \phi_{syn}$, which can be calculated by the difference of the phase measurements made at each of the two single wavelengths and then adding $2\pi$ to the result whenever $\Delta \phi_{syn}$ is less than zero. $\Delta \phi_{syn}$ is the phase one would obtain had $\Lambda$ been the actual illumination wavelength used and thus allows for wrap-free phase measurements of a large $\Delta x$. $\Delta \phi_{syn}$ can still suffer from phase wrapping, however, if $\Lambda$ is not chosen to be sufficiently large. It should also be noted that the noise level in the synthetic wavelength phase map can suffer from noise magnification due to amplification by $\Lambda$, as is discussed herein below.

In OCT, $\lambda_1$ and $\lambda_2$ can correspond to the center wavelengths of two different subsets of the broadband source spectrum. The broadband spectrum acquired during SD-OCT imaging can be divided by applying Gaussian windows to different portions of the spectrum as shown in FIGS. 1a through 1d. The spectrum can first be interpolated to be evenly spaced in wavenumber (See, e.g., FIG. 1a). The DC components of the signal can be isolated by low pass filtering the k-space spectrum (See, e.g., FIG. 1b). The raw spectrum can then be divided by the DC spectrum which leaves the interferometric term from Eq. (1) (See, e.g., FIG. 1c). The Gaussian windows can be applied to the remaining interference signal (See, e.g., FIG. 1d). The resulting signals can have the form $$i_1(k) \propto e^{\frac{-(k-k_1)^2}{\Delta k_1^2}} \cos(2kn(x+\Delta x)) \tag{5}$$

$$i_2(k) \propto e^{\frac{-(k-k_2)^2}{\Delta k_2^2}} \cos(2kn(x+\Delta x))$$

with $k_1 < k_2$ being the centers of the two Gaussian windows and $\Delta k_1$ and $\Delta k_2$ as their bandwidths. Although in principle the windows may be of any desirable shape, Gaussian windows offer a convenient spectral shaping tool due to their Fourier transform properties and for their ability to suppress sidelobe artifacts, allowing for separation of closely spaced reflectors. A potential side effect is that spectral reshaping can also decrease the SNR in OCT images, which can affect the phase stability. Applying the windows in the described manner can allow the resulting spectra to be Gaussian shaped regardless of the form of the original spectrum. Performing a Fourier transform separately to the two windowed spectra can yield phase information at two different center wavelengths.

Extending this analysis to three or more windows can be done iteratively by calculating a new synthetic between the synthetic wavelength defined in Eq. (4) and a third wavelength. This analysis can thus be extended to an arbitrary number of additional wavelengths.

It is to be understood that the steps described in the previous paragraphs for windowing the OCT signal into two or more spectral regions for the purpose of generating a synthetic wavelength signal are exemplary. Variations or simplifications of these steps are also possible and do not differ from the essence of the presently disclosed subject matter. For example, interpolation of the signal data from being evenly spaced in wavelength to evenly spaced in wavenumber can be done at any stage in the windowing process or not done at all if accurate depth sampling after the Fourier transform is not required. Similarly, alternate steps may be substituted for generation of the DC spectrum and using it to correct the raw signal spectrum. For example, the DC spectrum can also be generated from the average of many raw signal spectra acquired at different lateral sample locations, and the DC spectrum may alternatively be subtracted from the raw signal spectrum. Also, in some cases it may not be necessary to correct the raw signal spectrum with the DC spectrum at all. There are many possible approaches, which are well known to those familiar with signal processing for windowing spectral data which include variations on the particular details described here.

As noted above, Gaussian windows are advantageous for dual-wavelength phase unwrapping as a particularly convenient form of OCT theory depends upon Gaussian shaped spectra. The source shape can affect the values calculated using phase and displacement relationships, and non-Gaussian sources can cause SNR loss and result in incorrect measurements of displacement values. Although Gaussian windows are a preferred aspect, many other window shapes (e.g., rectangular, sine, or cosine) may also be used. The windowing can be performed after wavelength-to-wavenumber conversion, if necessary, in the signal processing chain.

In the shot-noise limit, the phase sensitivity, $\delta\phi$, of a reflector in an acquired OCT interferogram can be described by the following equation:

$$\delta\varphi = \frac{2}{\pi}(SNR)^{-\frac{1}{2}} \quad (6)$$

and the SNR can be described as follows:

$$SNR = \frac{\Delta t \int \rho(k) R_s(k) S(k) dk}{2e} \quad (7)$$

where $\rho(k)$ is the detector responsivity, $S(k)$ is the spectral density function detected, $\Delta t$ is the integration time, and $e$ is the electronic charge. The SNR used here is the SNR of the sample reflector of interest, which determines the sensitivity of the phase measurement. The phase sensitivity can be converted to a displacement sensitivity by combining Eq. (6) with Eq. (3) for m=0, giving the following relationship:

$$\delta x = \frac{\lambda_0 \delta\varphi}{4\pi n} \quad (8)$$

Several important observations can be made regarding Eqs. (6), (7), and (8). $\delta\phi$ depends upon the integrated power at the detector, and $\delta x$ is affected both by $\delta\phi$ and $\lambda_o$. Each of the two spectra produced by windowing has phase noise, $\delta\phi_1$ and $\delta\phi_2$, respectively. Because $\Delta\phi_{syn}=\phi_1-\phi_2$, the synthetic wavelength phase noise, $\delta\phi_{syn}$ depends on a quadrature addition of the noise levels of each spectra. The noise of each of the two spectra is correlated according to the amount of overlap of the two windows, which can be described by their covariance. Thus, the synthetic wavelength has a phase noise given by the following:

$$\delta\phi_{syn} = \sqrt{\delta\phi_1^2 + \delta\phi_2^2 - cov(\delta\phi_1^2, \delta\phi_2^2)} \quad (9)$$

where $cov(\delta\phi_1, \delta\phi_2)$ is the covariance of the phase noise between the two spectra. As a first simple model for the covariance, the following can be assumed:

$$cov(\delta\phi_1^2, \delta\phi_2^2) = a(k)(\delta\phi_1^2 + \delta\phi_2^2) \quad (10)$$

in which a(k) is a function describing the amount of overlap of the two Gaussian windows described as follows:

$$a(k) = \frac{\int_{-\infty}^{\beta} i_2(k) dk + \int_{\beta}^{+\infty} i_1(k) dk}{\frac{1}{2}\int_{-\infty}^{+\infty} [i_1(k) + i_2(k)] dk} \quad (11)$$

with $\beta=(k_1\Delta k_2+k_2\Delta k_1)/(\Delta k_1+\Delta k_2)$ being the point at which the two windows intersect. If it is assumed that $\Delta k_1=\Delta k_2$, then as $$\lim_{k_1-k_2} \to 0, a(k) \to 1$$

corresponding to complete overlap of the two windows. In this case, $\delta\phi_{syn}=0$ as $cov(\phi_1^2,\phi_2^2)=\phi_1^2+\phi_2^2$. If the two windows are greatly separated, a(k)=0, indicating that $\delta\phi_{syn}$ is equal to $\delta\phi_1$ and $\delta\phi_2$ added in quadrature.

Windowing the original spectrum reduces both the bandwidth and SNR:

$$SNR = \frac{\Delta t \int \rho(k) R_s(k) S(k) e^{\frac{(k-k_1)^2}{\Delta k^2}} dk}{2e} \quad (12)$$

where the Gaussian in the integrand is centered at $k_1$ and has a bandwidth of $\Delta k$. The SNR of the windowed spectrum is lower than that of the original spectrum. This can effectively degrade $\delta\phi_{syn}$, and the reduced bandwidth can result in a loss of axial resolution in each of the images generated from the windowing procedure. It can be desirable to use broad windows to preserve the axial resolution. If the synthetic wavelength $\Lambda$ were to replace $\lambda_o$ in Eq. (8) and $\delta\phi_{syn}$ replaced $\delta\phi$, the synthetic wavelength displacement sensitivity, $\delta x_{syn}$, can be given as follows:

$$\delta x_{syn} = \frac{\Lambda \delta\varphi_{syn}}{4\pi n} \quad (13)$$

Important considerations can include the choice of the window width and the center wavelength of the window. Wrapping will occur if the difference between two consecutive measurements is greater than $\Lambda/2$. Thus, because as $$\lim_{|\lambda_1-\lambda_2|} \to 0,$$

$\Lambda$, continuously increases, larger displacements can be resolved by choosing two windows closer together. For instance, the largest possible displacement measurement of the sample can determine the maximum window separation according to the following:

$$\Delta x_{max} = \frac{\Lambda}{4n} \quad (14)$$

This displacement is the largest motion that can be resolved before phase wrapping occurs. Although such movement would give a large $\Lambda$ allowing for resolution of large displacements, doing so can also increase the SNR of each windowed spectra by integrating over a larger area of the spectral density function. It is noted, however, that $\delta\phi_{syn}$ also scales with $\Lambda$ (See, e.g., Eq. (13))

In contrast, the minimum resolvable displacement, $\Delta x_{min}$, can be given by the following:

$$\Delta x_{min} = \frac{\Lambda \delta\varphi_{eq}}{4\pi n} \quad (15)$$

where $\delta\phi_{eq}$ is the phase sensitivity of the system. The phase sensitivity can be related to the SNR of the system by the following relationship:

$$\delta\varphi_{eq} = \frac{2}{\pi}(SNR)^{\frac{1}{2}} \quad (16)$$

where the shot-noise limit is assumed.

It is important to note the distinction between $\delta\phi_{syn}$ and $\delta x_{syn}$ in this analysis. $\delta\phi_{syn}$ approaches 0 as the separation between the windows decreases because the synthetic phase is based upon the difference between the measured phases of each window. When the windows are completely overlapped, they possess complete correlation and thus their covariance is equal to the sum of their variances, which from Eq. (9) yields $\delta\phi_{syn}=0$. However, $\delta x_{syn}$ is not zero because $\Lambda$ approaches $\infty$ in this case. For situations where window separation is large, $\Lambda$ becomes small while $\delta\phi_{syn}$ becomes large because the SNR of the windowed spectra degrades with increasing distance from the source center. Thus, $\Lambda$ and $\delta\phi_{syn}$ act to balance each other, keeping $\delta x_{syn}$ non-zero and finite.

Figure 2:
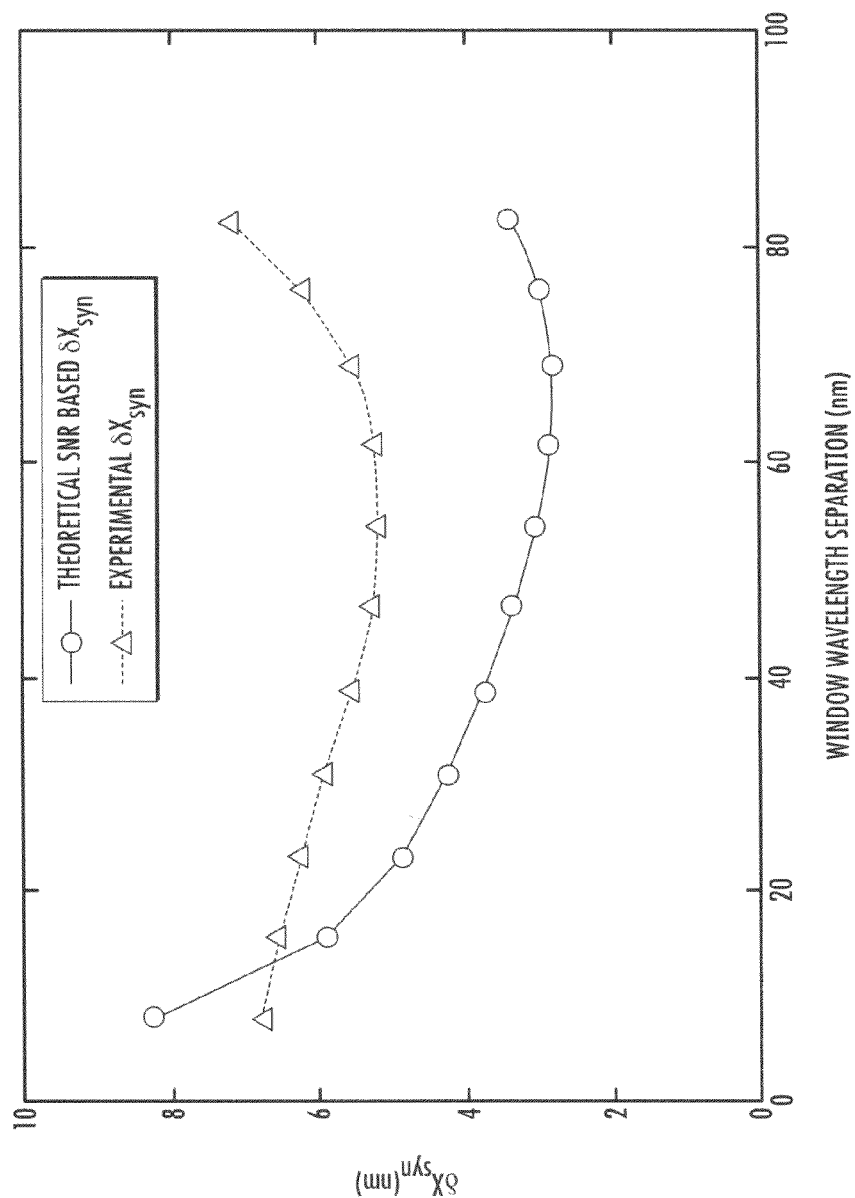
FIG. 2 is a graph showing the effects of varying window wavelength separation on the synthetic wavelength displacement sensitivity.

These observations indicate that the optimal choice of window placement over the original spectrum is determined by balancing the separation of the windows about the source center such that $\Lambda$ is sufficiently large to unwrap expected phase jumps and yet still maintains sufficient phase stability to keep $\delta x_{syn}$ low. FIG. 2 illustrates the results of an example of such an analysis, in which Experimental data was obtained from the surface of a glass coverslip as described below. Equation (13) can plotted theoretically using Eq. (9) and the SNR dependent expressions to determine $\delta\phi_{syn}$. The measured SNR for the lower wavelength window decreased from 46.3 dB to 39.4 dB, while that of the higher wavelength window decreased from 46.6 dB to 43 dB as the wavelength separation increased. Because the power of the source was less concentrated for wavelengths far from the source center, the strength of the interference fringes was also reduced at these wavelengths. Experimentally, $\delta\phi_{syn}$ is determined by the standard deviation of the $\Delta\phi_{syn}$ measurements.

FIG. 2 shows that $\delta x_{syn}$ increases (resolution degrades) as the two windows are moved very close together or very far apart. It is noted that both the independently measured displacement sensitivity and the SNR-calculated sensitivity follow the same general trend for windows that are separated by more than 20 nm. The theoretical model does not, however, correctly predict the experimental trend of $\delta x_{syn}$ for highly overlapped windows ($|\lambda 1-\lambda 2|<20$ nm) as $\delta\phi_{syn}$ does not decrease fast enough to balance the rapid increase in $\Lambda$. The covariance model in Eqs. (10) and (11) could be an oversimplification of the process governing the effects of window overlap.

Another important consideration is that the coherence length for each of the resulting windows remains the same in order to ensure proper comparison of the phase at each pixel in depth. Because the synthetic wavelength method relies upon pixel to pixel comparisons between the two phase maps generated from windowing, differences in the coherence lengths can cause the location of a scatterer to shift resulting in errors in the synthetic phase measurement.

A further consideration is the shape of the windowed spectra. Gaussian spectra can be useful to obtain a correct phase-displacement relationship, whereas a non-Gaussian spectrum can result in phase data that is not entirely accurate after the Fourier transform. Therefore, the DC spectrum can be divided out of the source from the acquired OCT spectrum, and the two separate windows can be applied to the remaining data. This process can yield two Gaussians at separate center wavelengths. Taking a Fourier transform of each of these resulting spectra can yield the phase information needed. An alternative to dividing out the DC spectrum would be subtracting the DC spectrum from each acquired spectrum.

The wavenumber spectrum can also be corrected for dispersion before windowing takes place. Even slight dispersion imbalances between different wavelengths can cause errors in the dual-wavelength algorithm. This allows for windows over wavelengths further from the source center to be used. Methods for dispersion correction either as part of or subsequent to wavelength-to-wavenumber conversion, such as a Hilbert-based dispersion algorithm, have been previously disclosed.

Further, the noise level $\delta\phi_{syn}$ can be reduced to that of $\delta\phi_o$ by using the synthetic wavelength image as a reference for correctly unwrapping the single wavelength image. After unwrapping using the synthetic wavelength method, the correct $\Delta x$ in Eq. (3) can be determined but can contain a high level of noise. Simply dividing the synthetic wavelength result by an integer number of $\lambda_o/2$ can allows for calculation of the appropriate value of m. This calculation can allow the data to be recast in terms of the source center wavelength. The correctly unwrapped image can have the same level of noise as is expected in the single wavelength case. However, areas of the image that possess noise levels of $\delta x > \lambda_o/4$ could cause a miscalculation of m resulting in spikes at these locations throughout the single wavelength corrected image. These spikes can be within +/−1 wrap and can be removed through a more simple unwrapping technique or filtering.

Based on the relationships discussed above, a two-window method for can be performed for phase unwrapping of OCT data. First, raw OCT spectrum data can be acquired (e.g., using a spectrometer). The data can be interpolated to be evenly spaced in k. Compensation can be made for any dispersion in the data, either as part of the interpolation of the data or as a separate process. The interpolated data can be processed to obtain a DC spectrum, such as by performing a Fourier transform, passing the data through a low-pass filter to isolate the DC components of the signal, and performing an inverse Fourier transform. The raw spectrum can be compared to the DC spectrum (e.g., by dividing by or subtracting the DC spectrum) to generate an interference signal. Multiple different windows (e.g., two Gaussian windows) can be applied to resulting interference fringes, and further signal processing (e.g., Fourier transforms) can be performed separately to each of the newly formed spectra. Phase information can then be extracted from each processed signal. One dataset can be subtracted from the other, and a value of $2\pi$ can be added if the difference is less than zero. The resulting phase data should be unwrapped according to the equivalent wavelength. Conversion of the phase difference to a physical displacement measurement can be obtained by substituting $\Lambda$ and $\Delta\phi_{syn}=\phi_1-\phi_2$ into Eq. (3). Reducing the level of noise in the image can then be accomplished by dividing the resulting displacement profile by an integer number of $\lambda_o/2$ and then adding the corresponding amount of wraps to the single wavelength data.

Figure 3:
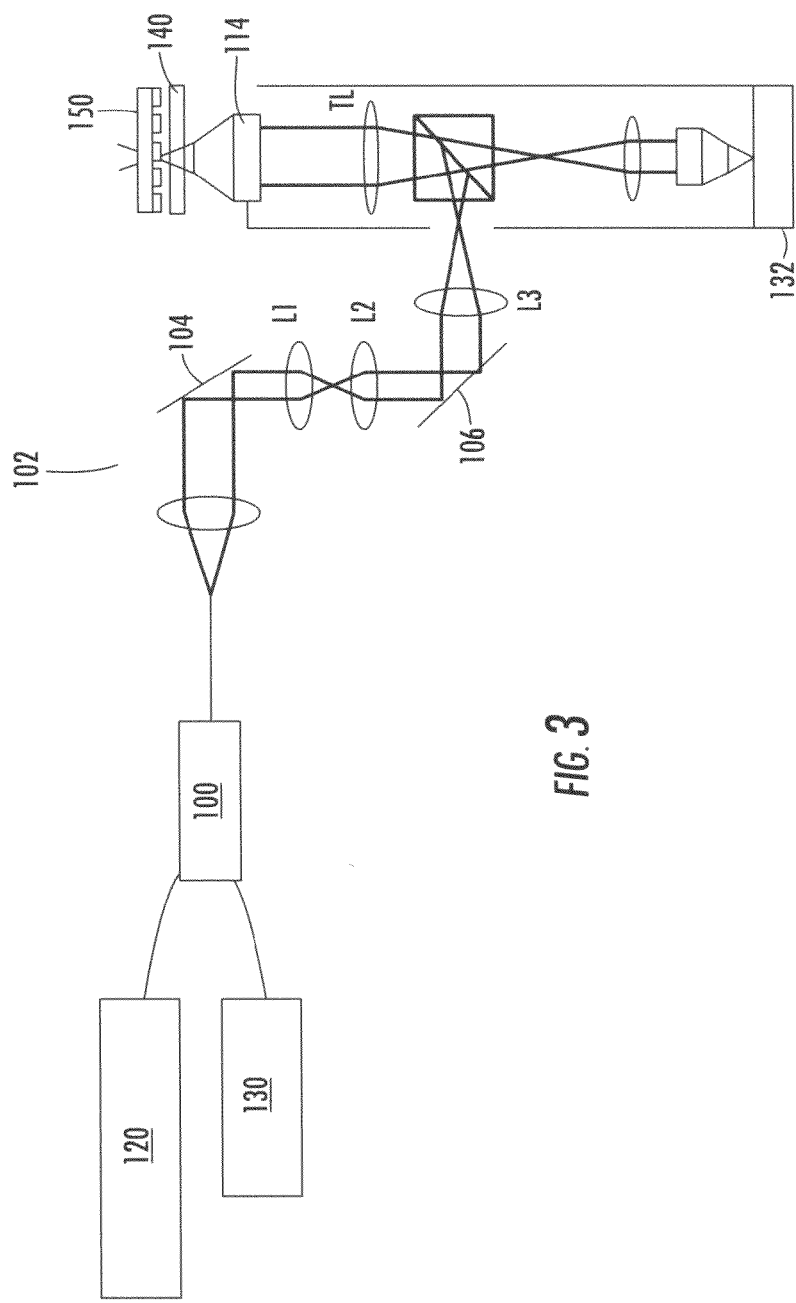
FIG. 3 is a schematic of a SDPM microscope that can be used during the dual-wavelength unwrapping procedure according to an aspect of the subject matter described herein.

In one particular example, the method described hereinabove can be implemented using a SDPM microscope shown in FIG. 3. The apparatus can consist of an interferometer 100 (e.g., a fiber based Michelson interferometer) with a sample arm 102 inserted via a documentation port 112 into an inverted microscope 110 (e.g., Zeiss Axiovert 200). A laser (e.g., a modelocked Titanium-Sapphire laser, such as a Femtosource laser produced by Femtolasers, Inc., having $\lambda_o$ at about 790 nm and $\Delta\lambda$ at about 70 nm) can serve as a source 120, allowing for an axial resolution of about 5.7 µm in air. A spectrometer 130 can use a linescan CCD 132 (e.g., Atmel, AVIVA, 2048 pixel, 19 kHz). Sample arm 102 can contain two galvo mirrors 104 and 106 to allow raster scanning of the sample and a series of lenses (e.g., imaging lenses L1, L2, and L3, and a tube lens TL). A microscope objective 114 (e.g., Zeiss, 40×, 0.6 NA) can focus light onto the sample giving a lateral resolution with a diffraction limit of about 1.6 µm. Such an objective 114 can be capable, for example, of resolving the smallest bars on a USAF test chart with 4.4 µm spacing per line pair (~2.2 µm per bar) in good agreement with the expected resolution. The signal data of the sample can be communicated to an OCT processor 200 in communication with a computer 210 for analyzing the signal data.

The effects of windowing on the noise of the synthetic wavelength image can be analyzed by placing a glass coverslip 140 (e.g., about 150 µm thick) in the sample arm and acquiring about 500 Å-scans at a single point with 150 µs integration time per A-scan. Following the synthetic wavelength windowing procedure described above, dual Gaussian windows with 40 nm bandwidths can be applied to each of the original spectra, the windows being equidistant from the source center. The synthetic phase can be calculated by taking a difference of the phase measurements obtained from Fourier transformation of each pair of windows. This procedure can be repeated for various values of $\Lambda$. The phase stability can be measured experimentally by taking the standard deviation of $\delta\phi_{syn}$ at the peak pixel location of the top coverslip surface in the A-scan profile. $\delta x_{syn}$ can be calculated using the measured phase stability in Eq. (13). Theoretically, the phase stability depends on the SNR, which can be calculated by taking the intensity at the A-scan peak squared divided by the variance of the noise floor over a region near the coverslip surface peak. The theoretical $\delta x_{syn}$ can be calculated by combining Eqs. (6), (9) and (13). FIG. 2 shows exemplary results of this kind of analysis.

Alternatively, the phase stability of the system can be measured by focusing light from source 102 onto the top surface of glass coverslip 140 (e.g., about 180 µm thick). Interference between reflections from the bottom and top surface can produce a single A-scan peak after k-space interpolation and Fourier transform of the resulting spectral interferogram. The standard deviation of the phase of this peak can be monitored over 1000 lines, which can result in about 167 pm for the temporal sensitivity at a single point on coverslip 140 and about 1.5 nm sensitivity for lateral scanning over the surface.

The dual-wavelength unwrapping method discussed above can be applied to data obtained by laterally scanning the sample beam across the surface of a calibration step grating 150 (e.g., Mikromasch TZ011, about 10 µm pitch, about 1.5 µm step height). In addition, AFM profiling of grating 150 can be performed to compare the results. By way of specific example, the dual-wavelength method can be applied to beating cardiomyocytes adhered to coverslip 140, and the phase can be measured during the contraction of a cell. Micron scale motion can be expected based on volume conservation of the cell volume. Further, electrical stimulation can be applied to the cells and correlated with image acquisition.

Figure 4:
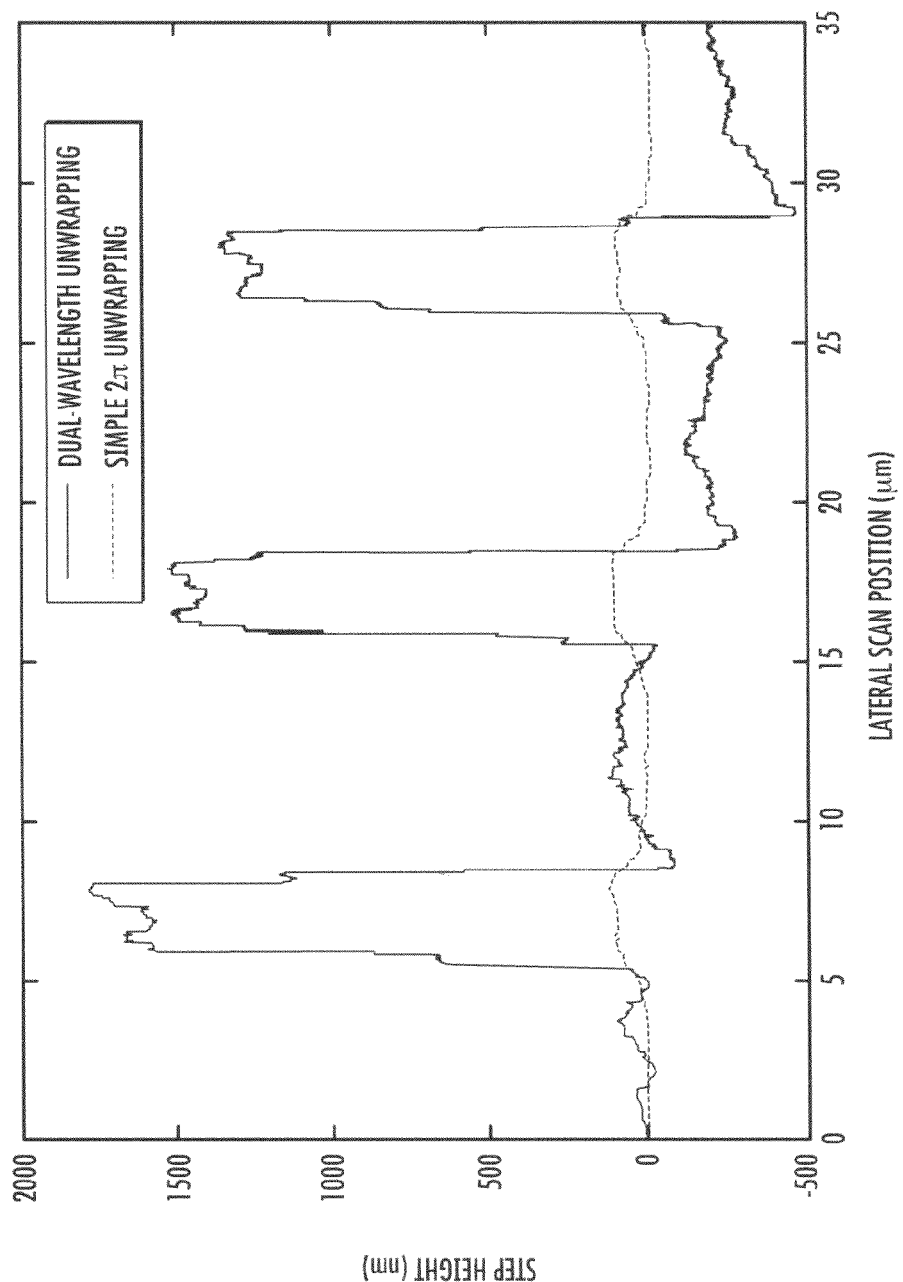
FIG. 4 is a graph illustrating cross-sectional profiles of the surface of an AFM calibration step grating comparing the average step height of a standard Matlab unwrapping procedure to a dual-wavelength unwrapping procedure according to an aspect of the subject matter described herein.
Figure 5:
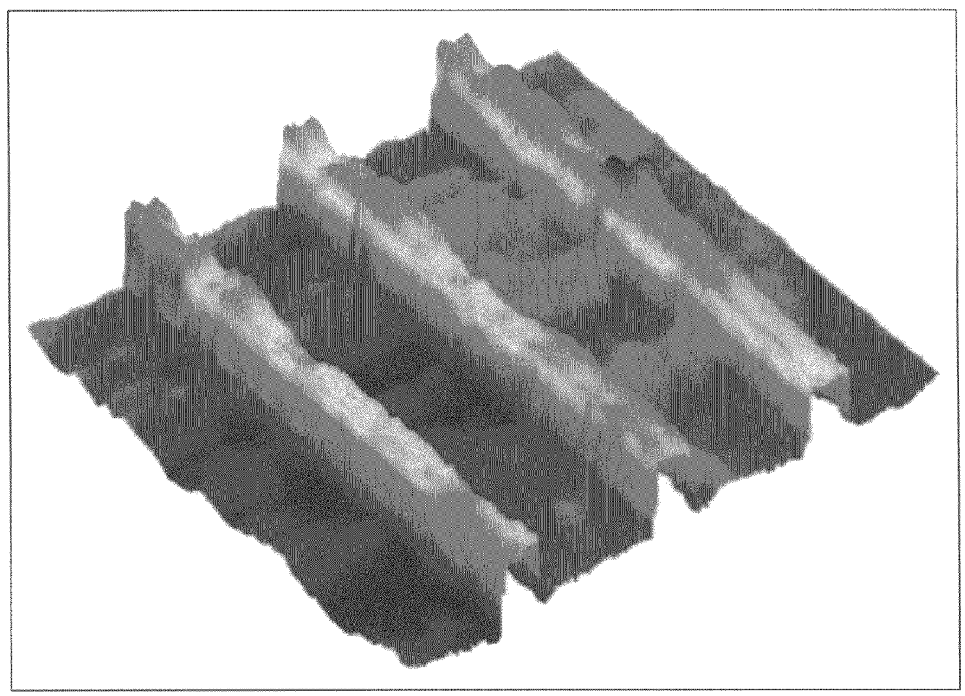
FIG. 5 is an OCT surface profile of a step grating obtained using synthetic wavelength unwrapping according to an aspect of the subject matter described herein.
Figure 6:
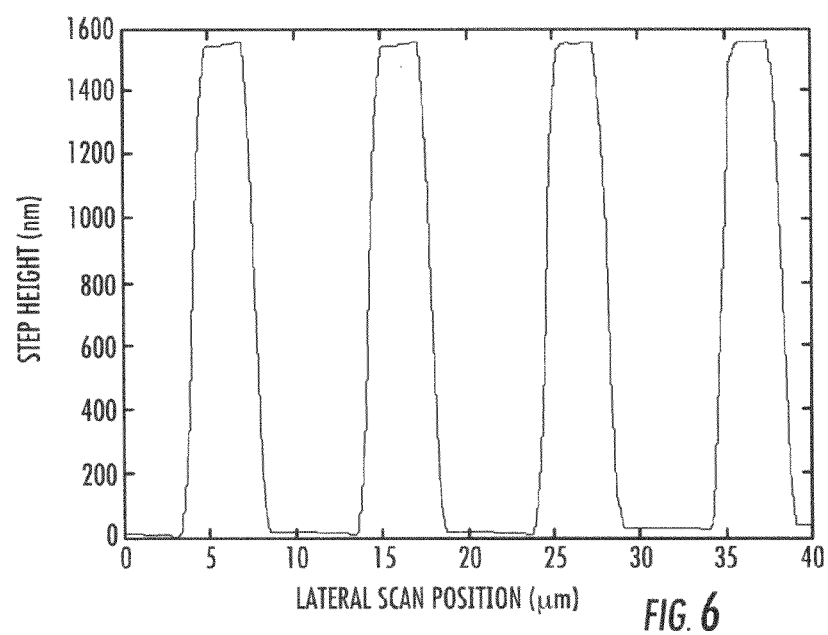
FIG. 6 is an AFM profile of a step grating used to perform the dual-wavelength unwrapping procedure according to an aspect of the subject matter described herein.

Referring to FIG. 4, results of an exemplary phase unwrapping of a surface profile taken from calibration step grating 150 is shown. The dual-wavelength method correctly measures an average step height of 1.50 µm. By comparison, unwrapping performed by a standard Matlab algorithm only measures an average step height of 70 nm. A 3D surface profile is shown in FIG. 5. AFM profiling of grating 150 (e.g., using a Digital Instruments 3100, with 0.5 Å height resolution) can measure an average step height of 1.52 µm and is shown in FIG. 6. These results show that the use of a synthetic wavelength can correctly unwrap a phase profile, even in the presence of multiply wrapped phase.

In another particular example, an atomic force microscope (AFM) calibration grating 150 can be used to validate the synthetic wavelength technique. The grating can be spaced 150 µm away from coverslip 140 surface to avoid phase corruption effects. This can cause a loss in signal due to the coverslip's distance away from the axial focus. Calculating the loss of intensity for backscatterers away from the focal plane can reveal a loss in SNR of about −84 dB. Using Eq. (7), the theoretical sensitivity of our system for a perfect reflector can be calculated using $\rho$=0.9 with 25 mW power in the sample arm at 150 µs integration time, yielding a sensitivity of about 130 dB. This can allow detection of reflectors beyond the depth of focus of objective 114.

Again, the synthetic wavelength unwrapping method can be applied to data obtained by laterally scanning the sample beam across the surface of the calibration step grating, which can consist of $SiO_2$ steps coated with $Si_3N_4$ on a silicon wafer, to obtain a dataset consisting of 100×50 A-scans covering a 20×6 µm area with an integration time of 150 µs. The 1.5 µm step height can be roughly twice the center wavelength of the source and yet can be less than its coherence length. Thus, grating 150 can be expected to produce multiple wrapping artifacts in the phase data.

The index of refraction for $Si_3N_4$ can have a trivial complex component at about 790 nm, implying normally incident light undergoes a $\pi$ phase shift upon reflection. However, the index of refraction of silicon at 790 nm (n=3.673 and k=5×10−3) could potentially cause a non-$\pi$ phase shift in reflected light. The phase shift deviation from $\pi$ for light incident upon a silicon surface from air may be describe as follows:

$$\Delta\varphi_{Si} = \pi - p \tag{17}$$

$$p = \tan^{-1}\left(\frac{2n_0 k_1}{n_1^2 + k_1^2 - n_0^2}\right) \tag{18}$$

where $n_o$=1 is the index of air, $n_1$=3.673 is the real component of the index of silicon, and $k_1$=5×10$^{-3}$ is its imaginary index. The value of $\rho$ can be calculated to be less than 1 mrad, which is much less than the phase difference caused by the calibration grating step height (approximately 400 mrad at the synthetic wavelength). Thus, the difference in materials between the peaks and valleys on the grating can not be expected to affect the phase measurement significantly.

FIG. 7a shows the raw, wrapped phase data obtained from the calibration step grating. FIG. 7b shows results of the synthetic wavelength unwrapping. Two Gaussian windows were used with 50 nm bandwidths using $\Lambda$=41 µm. The phase of the peak pixel location in an A-scan corresponding to the peak surface of the grating for each spectrum was used to calculate $\Delta\phi_{syn}$ and yielded an SNR of 32.3 dB and 33.0 dB for the lower and higher wavelength windows respectively. The step height was measured by taking the difference of the average peaks and valley of the grating as outlined in FIG. 7b. The standard deviation over the valley indicated was 116 nm. The dual-wavelength method correctly measures an average step height of 1.51+/−0.14 µm. FIG. 7c shows a cross-sectional profile of the grating comparing the synthetic wavelength result with unwrapping performed by a simple one dimensional $2\pi$ addition/subtraction algorithm from Matlab. The Matlab algorithm only measures an average step height of 70 nm due to the method's inability to correctly detect multiple wrapping. AFM profiling of the grating (Digital Instruments 3100, 0.5 Å height resolution) measured an average step height of 1.52 µm. This confirms that using a synthetic wavelength can correctly unwrap a phase profile, even in the presence of multiply wrapped phase. Using values for $\Lambda$ from 16.5 µm to 94.7 µm ($|\lambda_1-\lambda_2|$=40 nm to 8 nm, respectively) yielded similar results for the measured step height. Using a smaller $\Lambda$ resulted in underestimating the calculated step height, potentially due to errors in the phase measurement resulting from windowing the original spectral data far from the source center.

Matlab uses a simple algorithm that unwraps the phase by searching for phase discontinuities along a one dimensional path. If the phase jump between two neighboring pixels in an image is greater than $\pi$ or less than $-\pi$ this is interpreted as a wrap, and $2\pi$ is subtracted or added to smooth the phase profile. Thus, if more than one wrap is contained within the pixel, it will not be correctly unwrapped. It is also possible that a true absolute phase jump greater than $\pi$ will be misinterpreted and perceived by Matlab to be a wrap. Another scenario is that a true wrap may not be detected if the resulting phase change between neighboring pixels does not yield an absolute phase difference greater than $\pi$. Thus, unwrapping using the phase from two different pixels still results in an ambiguous phase measurement. The synthetic wavelength method only uses the information contained within a single data point to generate an unwrapped profile and can utilize a sufficiently large $\Lambda$ to ensure correct unwrapping. This is possible because of the broadband spectrum of the source and the ability to access its phase information by the Fourier transform. The phase at a single pixel in a given phase image can be measured unambiguously regardless of the phase in the surrounding pixels.

Figure 8B:
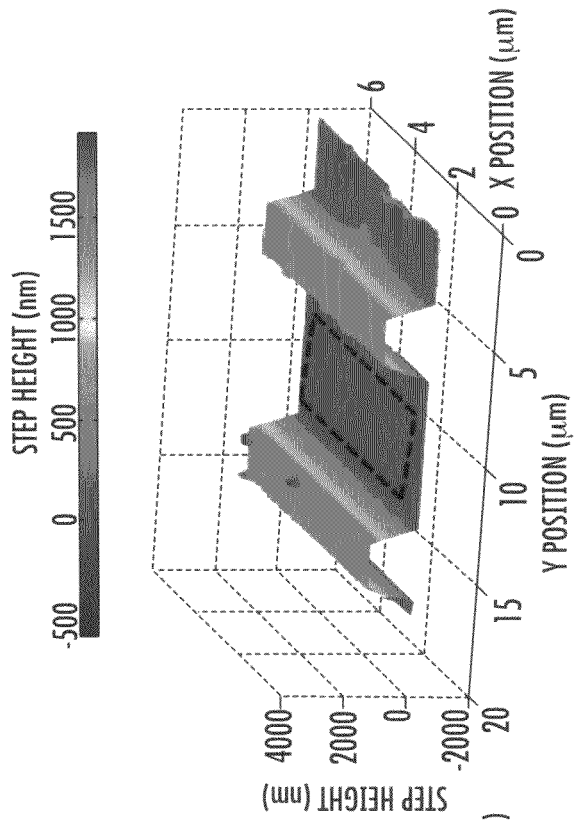
FIG. 8b is an OCT surface profile of a final corrected image according to an aspect of the subject matter described herein.
Figure 8A:
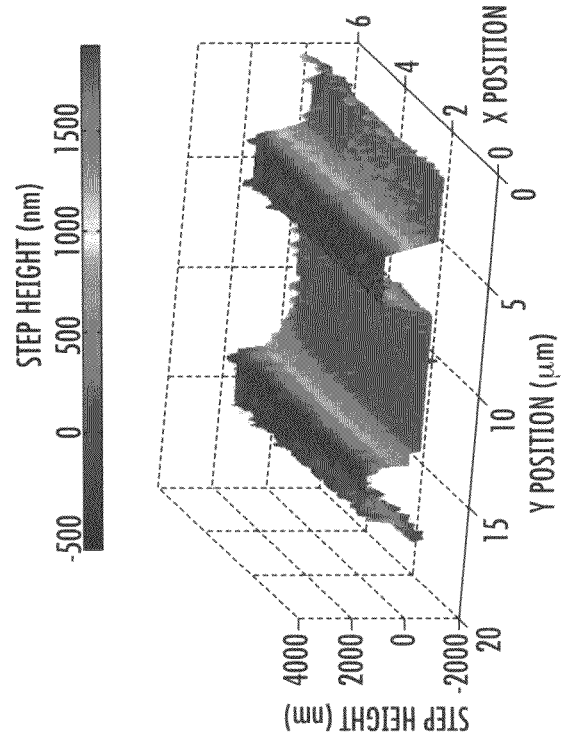
FIG. 8a is an OCT surface profile of a single wavelength corrected phase image of an AFM grating according to an aspect of the subject matter described herein.

Using the synthetic wavelength phase map as a reference, the original single wavelength image was corrected by dividing the synthetic wavelength image by $\lambda_o/2$ of the source to obtain an integer amount for m in Eq. (3). This result was then added to the single wavelength phase map to produce an intermediate image. The result in FIG. 8a shows regions throughout the dataset containing spikes or regions where the phase was incorrectly determined. The image was corrected by subtracting the intermediate image from the synthetic wavelength image and then adding +/-2π to areas of the difference map in excess of $|\pi|$. However, some spikes still remained in regions of the image containing high amounts of noise. These areas are within a +/-2π wrap (or equivalently, +/-λo/2) from the correct value and can be removed through a simpler software unwrapping method that searches for these sharp steps. A simple unwrapping filter consisting of a 3×3 window was used to compare the phase of the center pixel to an average of the phases of the neighboring pixels. If a phase difference in excess of $|\pi|$ was detected, then the center pixel was unwrapped by the addition or subtraction of 2π. The result of this step is shown in FIG. 8b. The noise level for the corrected image, taken as the standard deviation of the measure values in the valley of the grating, was 3 nm. The measured value for the average step height was 1.51+/-0.01 µm. Portions of the image in FIG. 8b contain noise artifacts that were unable to be removed by the unwrapping filter due to high noise levels in the image which corrupt the single wavelength image after correction. However, the amplified noise level introduced in the synthetic wavelength image was reduced to the single wavelength noise limit while measuring the correct step height in the presence of multiple wrapping artifacts.

Figure 9:
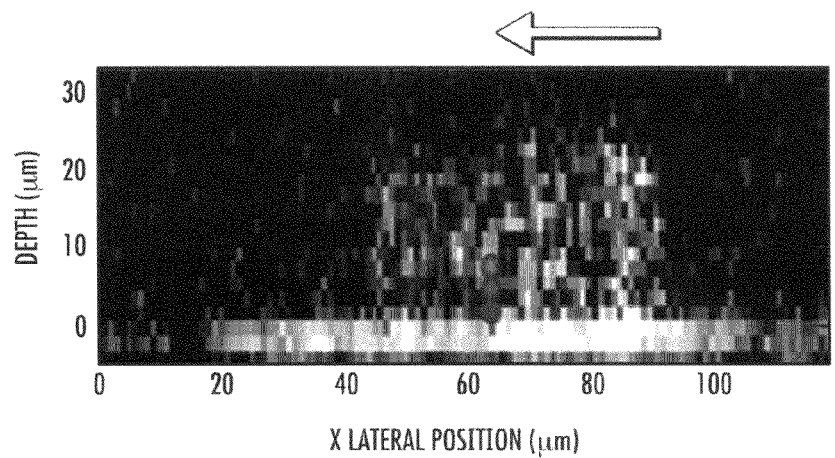
FIG. 9 is an OCT magnitude image of a cardiomyocyte adhered to the top of a glass coverslip on which the dual-wavelength unwrapping procedure can be performed according to an aspect of the subject matter described herein.
Figure 10:
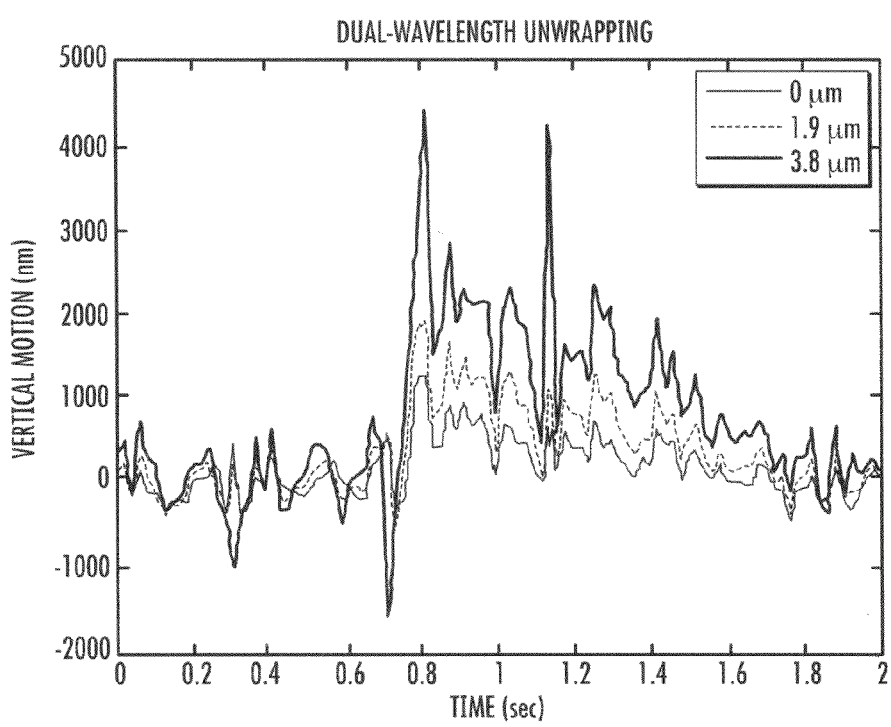
FIG. 10 is a graph showing measurement of cell motion at three points along an axial dimension during contraction as determined by the dual-wavelength unwrapping procedure according to an aspect of the subject matter described herein.

Synthetic wavelength unwrapping can also be applied to phase measurements from cardiomyocytes during contraction. Referring to FIG. 9, an OCT magnitude image of a cell is shown. The arrow indicates the direction of bulk cell motion curing a contraction, and the three dots correspond to locations of measured displacement shown in FIG. 10 (red dot corresponding to 0 µm, green dot corresponding to 1.9 µm, and blue dot corresponding to 3.8 µm). FIG. 10 shows a plot of the displacement as measured by the phase over time. Upon electrical stimulation, the cell can contract, resulting in upward motion of the cell membrane. The synthetic wavelength unwrapping can reveal motion on the order of several microns as the cell contracts.

Synthetic wavelength unwrapping can further be applied to phase measurements from human epithelial cheek cells. The cells were placed upon the top surface of a coverslip which had anti-reflective coating to help reduce the effects of phase corruption. The phase profile of a group of cells is shown in FIGS. 11a through 11c. Images consist of 1000×100 lines acquired using a 20× objective (NA=0.5, 1.9 µm spot size) to give a wider field of view for visualizing a group of cells. Initially a wrapped phase profile was obtained in FIG. 11a and was then unwrapped using the synthetic wavelength method with $\Lambda$=20.4 µm. As can be seen from the bright field microscope image in FIG. 11c, single cells as well as a cluster of cells stacked together were present. The cell cluster should be expected to introduce multiple wrapping artifacts due to its thickness whereas the single cells may produce only a single wrap. After applying the synthetic wavelength algorithm, noise reduction to the single wavelength image was performed. Additionally, a 3×3 median filter was used to smooth the image. A clear picture of the cell height above the coverslip surface is obtained in FIG. 11b. The heights of both single cells and the cell cluster are resolved with the regions of the original image containing either single or multiple phase wraps corrected. The standard deviation over the region indicated by the box in FIG. 11b was 31 nm for the synthetic wavelength image and 7 nm for the single wavelength corrected image demonstrating the effects of single wavelength noise reduction.

In summary, the subject matter herein presents a synthetic wavelength processing methods to allow for correct phase unwrapping in phase sensitive implementations of OCT. Using two spectral windows on the detected broadband spectrum allows phase information from different wavelengths to be obtained. The phase information can then be related to that of a longer synthetic wavelength to measure large phase jumps in a given sample that would normally induce phase wrapping. The two window method may potentially be extrapolated to use a continuous range of wavelengths, similar to, to allow even more robust phase unwrapping. This method may prove useful in other phase based implementations of OCT where phase wrapping is problematic, such as in Doppler or polarization sensitive OCT or in applications such as cellular imaging.

Although the above disclosure concentrates on the detailed technique for application of synthetic wavelength phase unwrapping in SDPM systems, one having skill in the art should understand that the technique is applicable to any form of low-coherence inteferometry which resolve phase, including all of the techniques mentioned herein above, including time-domain OCT among others.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A method for phase unwrapping of an optical coherence tomography (OCT) signal, the method comprising:
    acquiring raw OCT signal data;
    interpolating the raw OCT signal data to be evenly spaced in k;
    isolating a direct-current (DC) spectrum from the interpolated OCT signal data;
    comparing the raw OCT signal data to the DC spectrum to generate an interference signal;
    applying Gaussian windows to the interference signal to generate a first signal and a second signal;
    processing the first signal and the second signal;
    extracting phase information from each of the first signal and the second signal; and
    comparing the phase information of the first signal to the phase information of the second signal to produce unwrapped phase data, and adding $2\pi$ if the difference between the phase information of the first signal and the second signal is less than zero.

2. The method of claim 1, wherein isolating a DC spectrum comprises:
    performing a Fourier transform on the interpolated OCT signal data;
    isolating the DC components of the signal; and
    performing an inverse Fourier transform on the isolated DC components.

3. The method of claim 2, wherein isolating the DC components of the signal comprises passing the transformed signal data through a low-pass filter.

4. The method of claim 1, wherein comparing the raw OCT signal data to the DC spectrum comprises dividing the raw OCT signal data by the DC spectrum.

5. The method of claim 1, wherein comparing the raw OCT signal data to the DC spectrum comprises subtracting the DC spectrum from the raw OCT signal data.

6. The method of claim 1, wherein applying Gaussian windows to the interference signal comprises applying windows having substantially the same coherence length.

7. The method of claim 1, further comprising correcting for dispersion in the interpolated OCT signal data prior to processing the interpolated OCT signal data.

8. The method of claim 1, further comprising measuring a phase stability of the OCT signal.

9. A method for phase unwrapping of an optical coherence tomography (OCT) signal, the method comprising:
    acquiring raw OCT signal data;
    interpolating the raw OCT signal data to be evenly spaced in k;
    correcting for dispersion in the interpolated OCT signal;
    performing a Fourier transform on the interpolated OCT signal data;
    passing the transformed signal data through a low-pass filter to isolate the direct-current (DC) components of the transformed signal;
    performing an inverse Fourier transform on the isolated DC components to obtain a DC spectrum;
    dividing the raw OCT signal data by the DC spectrum to generate an interference signal;
    applying Gaussian windows to the interference signal to generate a first signal and a second signal;
    processing the first signal and the second signal;
    extracting phase information from each of the first signal and the second signal; and
    comparing the phase information of the first signal to the phase information of the second signal to produce unwrapped phase data, and adding $2\pi$ if the difference between the phase information of the first signal and the second signal is less than zero.

10. A system for phase unwrapping of an optical coherence tomography (OCT) signal comprising:
    a light source;
    a sample arm having optical elements configured to focus light from the source onto a sample;
    at least one spectrometer combined with at least one detector for acquiring OCT signal data from the sample;
    a data processor for processing the acquired OCT signal data, generating an interference signal, applying Gaussian windows to the interference signal to generate a first signal and a second signal, extracting phase information from each of the first signal and the second signal, comparing the phase information of the first signal to the phase information of the second signal to produce unwrapped phase data, and adding $2\pi$ if the difference between the phase information of the first signal and the second signal is less than zero.

11. The system of claim 10, further comprising a calibration step grating, wherein the at least one detector acquires OCT signal data from light focused onto the sample being laterally scanned across a surface of the calibration step grating.

12. A non-transitory computer program stored on a computer readable medium for causing a computer to execute an image processing method, the image processing method comprising:
    acquiring raw (optical coherence tomography) OCT signal data;
    interpolating the raw OCT signal data to be evenly spaced in k;
    processing the interpolated OCT signal data to obtain a direct-current (DC) spectrum;
    comparing the raw OCT signal data to the DC spectrum to generate an interference signal;
    applying Gaussian windows to the interference signal to generate a first signal and a second signal;
    processing the first signal and the second signal;
    extracting phase information from each of the first signal and the second signal; and
    comparing the phase information of the first signal to the phase information of the second signal to produce unwrapped phase data, and adding $2\pi$ if the difference between the phase information of the first signal and the second signal is less than zero.

* * * * *